United States Patent
Behroozi

(10) Patent No.: US 6,563,588 B2
(45) Date of Patent: May 13, 2003

(54) APPARATUS AND METHOD FOR MEASUREMENT OF FLUID VISCOSITY

(75) Inventor: Feredoon Behroozi, Cedar Falls, IA (US)

(73) Assignee: University of Northern Iowa Research Foundation, Cedar Falls, IA (US)

( * ) Notice: Subject to any disclaimer, the term of this patent is extended or adjusted under 35 U.S.C. 154(b) by 62 days.

(21) Appl. No.: 09/747,528

(22) Filed: Dec. 22, 2000

(65) Prior Publication Data

US 2002/0080362 A1 Jun. 27, 2002

(51) Int. Cl.⁷ .............................................. G01B 11/00
(52) U.S. Cl. ........................ 356/477; 356/482; 356/502
(58) Field of Search ................................. 356/477, 482, 356/496, 502; 250/227.19, 227.27

(56) References Cited

U.S. PATENT DOCUMENTS

| | | |
|---|---|---|
| 4,611,486 A | 9/1986 | Stockhausen |
| 5,303,030 A * | 4/1994 | Abraham et al. ........... 356/482 |
| 5,590,560 A | 1/1997 | Joos et al. |
| 6,412,354 B1 * | 7/2002 | Birchak et al. .......... 73/861.27 |

OTHER PUBLICATIONS

T. M Bohanan, J.M. Mikrut, B.M. Abraham, J.B. Ketterson, P. Dutta, "Fiber–Optic Detection System for Capillary Waves: An Apparatus for Studying Liquid Surfaces and Spread Monolayers", Rev. Sci Instrum. 62 (12), Dec. 1991.

Jackson, D. A. "Monomode Optical Fibre Interferometers for Precision Measurement", J. Phys. E: Sci Instrum. vol. 18, 1985.

A.P. Wallenberger and D.R. Lyzenga, "Measurement of the Surface Tension of Water Using Microwave Backscatter from Gravity–Capillary Waves", IEEE Transactions of Geoscience and Remote Sensing vol. 28, No. 6, Nov., 1990.

J.C. Earnshaw and C.J. Hughes, "High–Frequency Capillary Waves on the Clean Surface of Water", Langmuir 7, 2419 (1991).

K. Y. Lee, T. Chou, D.S. Chung, and E. Mazur, "Direct Measurement of the Spatial Damping of Capillary Waves at Liquid–Vapor Interfaces", J. Phys. Chem. 97, 12876 (1993).

A. Belmonte and J–M. Flesselles, "Experimental Determination of the Dispersion Relation for Spiral Waves", Phys. Rev. Lett. 77, 1174 (1996).

W. M. Klipstein, J.S. Radnich, and S. K. Lamoreaux, "Thermally Excited Liquid Surface Waves and Their Study Through the Quasielastic Scattering of Light", Am. J. Phys. 64, 758 (1996).

D.R. Howell, B. Buhrow, T. Heath, C. McKenna, W. Hwang, and F. M. Schatz, "Measurements of Surface–Wave Damping in a Container", Physics of Fluids vol. 12, No. 2 (2000).

* cited by examiner

Primary Examiner—Robert H. Kim
Assistant Examiner—Hoon K. Song
(74) Attorney, Agent, or Firm—Allan L. Harms

(57) ABSTRACT

A non-contact apparatus and method for mapping the wave profile of capillary waves on a fluid surface to determine viscosity of the fluid. Two conducting blades coupled to a sine wave generator are positioned spaced laterally above and near the surface of the fluid to generate a standing capillary wave on the fluid surface between the blades. A laterally moveable fiber optic probe is coupled to a laser to transmit laser light toward the fluid surface and to receive reflected light from the fluid surface. Part of the laser light reflects from the end of the probe and creates an interference pattern with the light reflected from the fluid surface. The light reflected from the end of the probe and from the fluid surface are combined to form an interference signal which is analyzed to obtain the amplitude of the wave directly under the probe. By moving the probe laterally, nodes on the standing wave may be detected to find the wavelength of the capillary wave. One blade may be decoupled from the sine wave generator and the fiber optic probe moved laterally to determine the wave amplitude of a traveling wave as a function of distance which is then used to determine viscosity.

23 Claims, 8 Drawing Sheets

APPARATUS AND METHOD FOR MEASUREMENT OF FLUID VISCOSITY

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The present invention pertains to non-contact measurement of fluid viscosity by use of a miniature laser interferometer.

BACKGROUND OF THE INVENTION

The invention is a new process for measuring the viscosity of fluids without making any physical contact with the fluid. Viscosity is a manifestation of fluid friction. The standard method for measuring viscosity was invented by the French physician Jean Louis Poiseuille (1799–1869) who devised the first flow viscometer. In the past two centuries many other eminent scientists, including James Clerk Maxwell, have tried their hands at inventing alternative viscometers. In principle all the current methods (Couette, falling-sphere, oscillating disk, and cone-and-plate viscometers) exploit the resistance experienced by an object in contact with and in relative motion to the fluid. While Stokes (1819–1903), father of modern fluid dynamics, recognized that the attenuation of surface waves could be exploited to measure viscosity without the use of a foreign object, no reliable method has been available to date.

U.S. Pat. No. 5,303,030 to Abraham et al. describes use of an optical interferometer for determination of surface tension of a fluid by reflecting a light beam off the surface of a fluid on which capillary waves have been induced. An optical fiber and a capillary wave inducing blade are held in a parallel fixed relation above the fluid surface. The capillary wavelength is determined by measuring the phase difference of the reflected signal at two points on the surface. The wavelength is then used to obtain the surface tension.

SUMMARY OF THE INVENTION

The determination of viscosity from the damping of capillary waves has been of great interest as it affords the possibility of a non-contact method for measuring viscosity. The instant invention provides a non-contact method and apparatus for precision measurement of the amplitude, wavelength, and attenuation of capillary waves on fluids. Surface waves on fluids, with wavelengths in the millimeter range, are known as capillary waves. In this wave regime surface tension and viscosity govern the propagation and attenuation of the surface waves while gravity plays a minor role. Therefore, data on dispersion and attenuation of capillary waves may be used to determine the surface tension and viscosity of fluids. Of particular interest has been the determination of viscosity from the damping of surface waves.

To obtain the wave profile of capillary waves the invention employs a fiber-optic detection system that functions as a miniature laser interferometer. The heart of the system consists of a single mode optical fiber, one end of which is positioned a short distance above the fluid surface. Laser light traveling through the optical fiber is partially reflected from the cleaved tip of the fiber and again from the fluid surface. The two reflected beams travel back through the same fiber forming an interference pattern. As the water level changes due to wave motion, the interference signal portrays an accurate record, in real time, of the variation of the gap between the end of the fiber optic cable and the fluid surface.

The invention obtains the wave profile with a resolution of about ten nanometers—some fifty times better than the resolution of a typical optical microscope. The invention has been used to obtain the dispersion and attenuation of capillary waves on pure water as a test case. Furthermore, the attenuation data has been used to obtain the viscosity of pure water as a function of temperature. Results using the invention are consistent with accepted values obtained by traditional flow viscometry thus demonstrating the great utility of this non-contact method for measuring viscosity.

The capillary waves are generated electronically by placing a metallic blade a few tenths of a millimeter above the water surface. A sinusoidal voltage of several hundred volts at a known frequency is applied between the blade and the water. Since water molecules are polar, the alternating electric field under the blade generates two capillary wave trains that recede from the blade on the two sides. Typically the amplitude of these waves is of the order of one micrometer.

To obtain the dispersion data, a standing wave is established on the fluid surface. A standing wave is generated when two blades, separated by a few centimeters, are used to generate waves of the same phase, amplitude, and frequency. Since each blade sends a wave train toward the other, a standing capillary wave is established on the water surface between the two blades. If the distance between the two blades is chosen to be a half odd-integer wavelength, the two wave trains interfere destructively on the outer sides of the blades. This judicious choice of the blades' separation produces a region of standing waves between the blades while the surface outside the blades remains calm. Measurement of the distance between nodes of the standing waves yields the wavelength of the capillary wave.

In the instant invention, the fiber optic probe is attached to a micro-positioner, which in turn is equipped with a digital micrometer. This enables measurement of the wavelength of the standing capillary waves routinely to within a micrometer. A precise dispersion relation is obtained by a measurement of the wavelength at various frequencies.

To obtain the attenuation data, a traveling wave is established on the fluid surface by using one blade. One fiber probe, held stationery on one side of the blade, provides the reference amplitude. The second fiber probe measures the amplitude of the wave as a function of distance away from the blade. The normalized amplitude attenuation data yields the viscosity of the fluid.

It is an object of the invention to provide a non-contact method and apparatus to precisely measure viscosity of a fluid.

It is a further object of the invention to provide a miniature laser interferometer system which may be used without mechanical contact with the fluid to determine the wave profile of capillary waves upon the surface of the fluid.

It is a further object of the invention to map the wave profile of a traveling capillary wave generated on a fluid surface.

It is yet another object of the invention to create a standing wave on a fluid surface which may be mapped by use of a laser interferometer.

It is still a further object of the invention to provide apparatus for non-contact measurement of the wave-length of a standing wave of varying frequencies generated on the surface of a fluid.

It is a further object of the invention to provide apparatus and a method to measure viscosity of a fluid without risk of contamination of the fluid under examination.

These and other objects of the invention will become apparent from examination of the description and claims which follow.

BRIEF DESCRIPTION OF THE SEVERAL VIEWS OF THE DRAWING(S)

Figure 7:
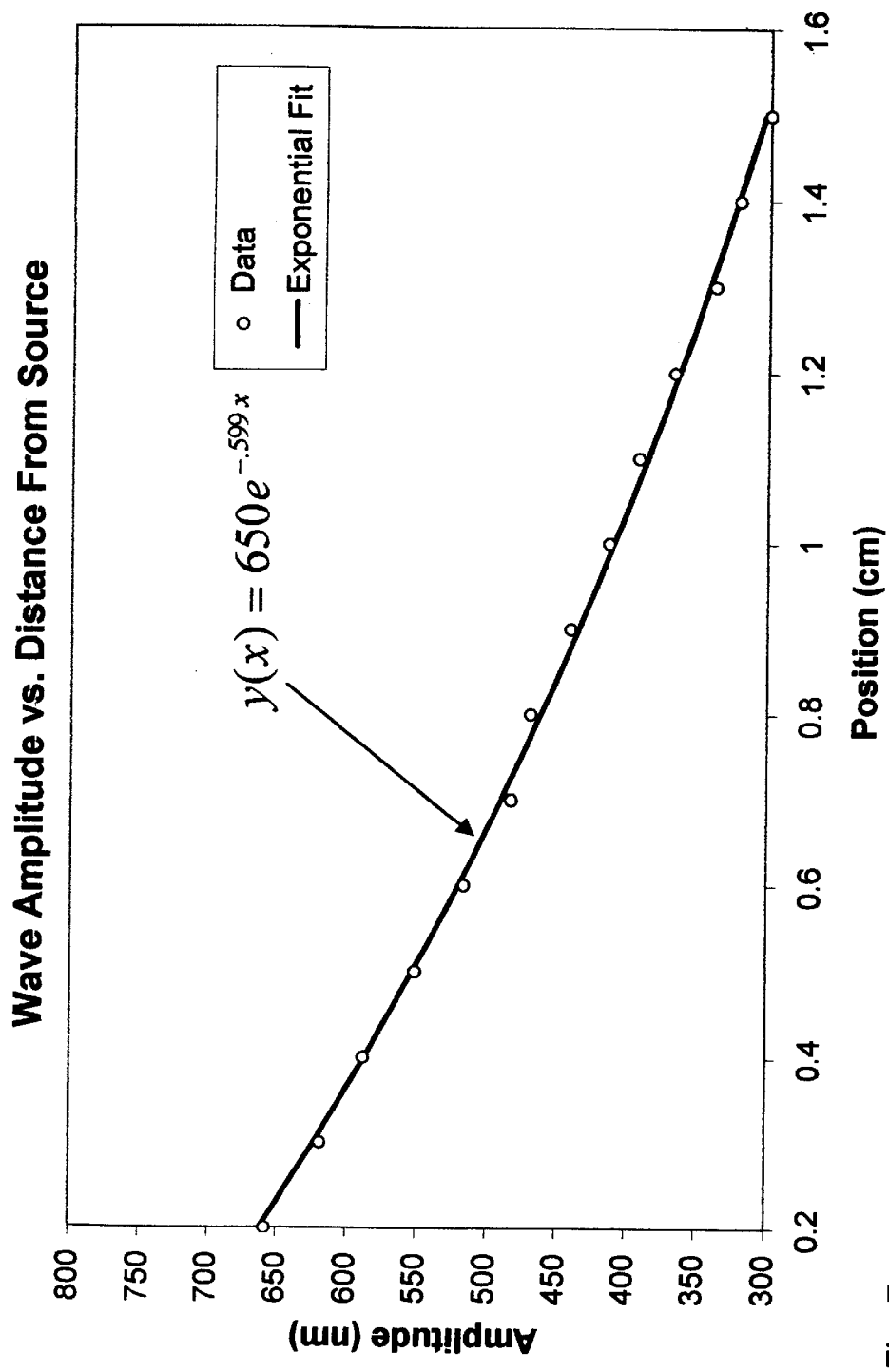

FIG. 7 is a graph showing wave amplitude vs. distance from the source as determined by the instant invention. The solid line is an exponential fit to the data. This plot yields a value of $8.9 \times 10^{-3}$ cm$^2$/s for the kinematic viscosity of water at 20° Celsius, in agreement with the accepted value obtained with conventional flow viscometry.

Figure 8:
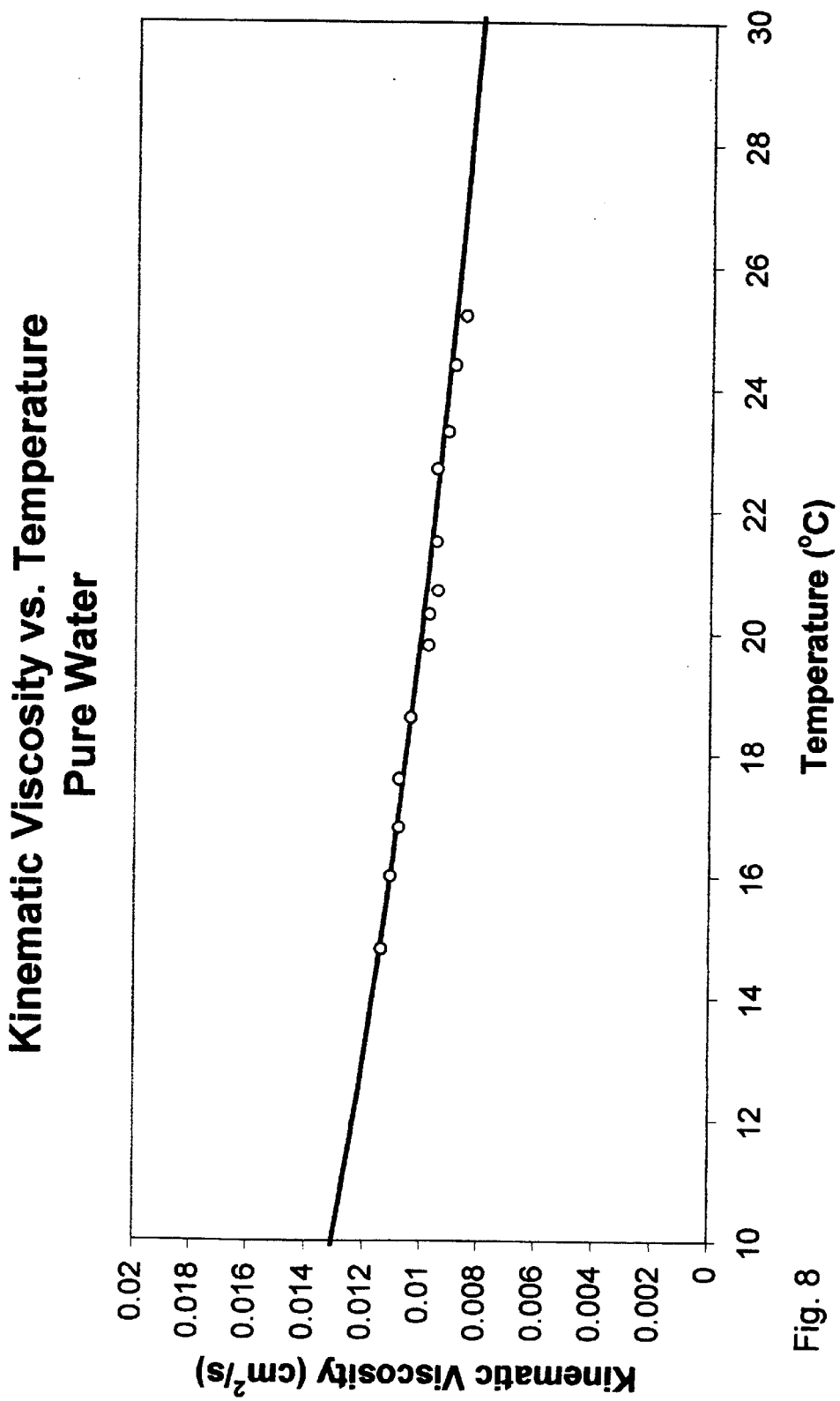

FIG. 8 is a graph showing data points for kinematic viscosity vs. temperature for pure water as determined with the invention method and apparatus. The data points are shown as open circles and the solid line represents the published data for kinematic viscosity of pure water as a function of temperature.

DETAILED DESCRIPTION OF THE INVENTION

Figure 1:
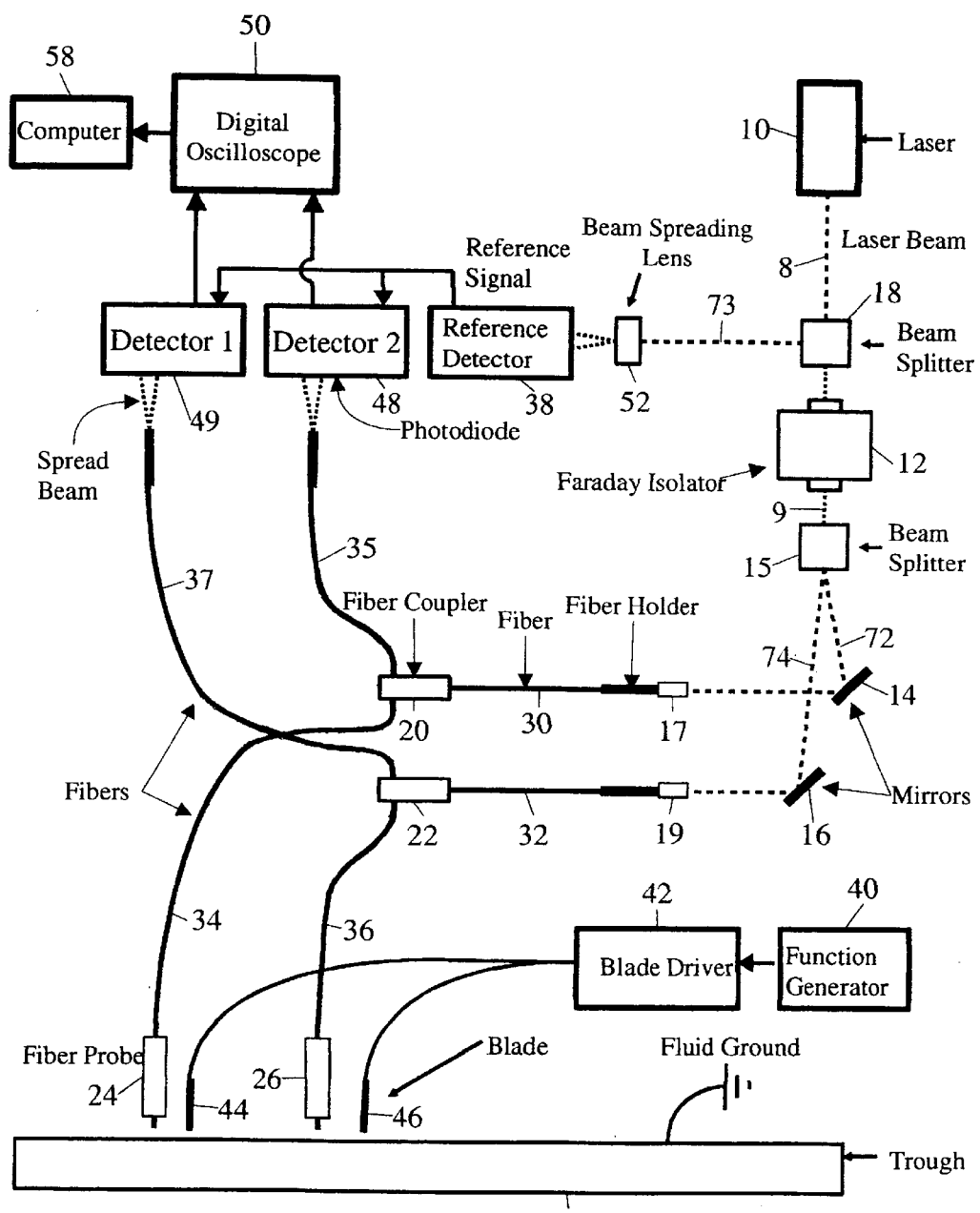
FIG. 1 is a detailed block diagram of the preferred embodiment of the invention apparatus.
Figure 2:
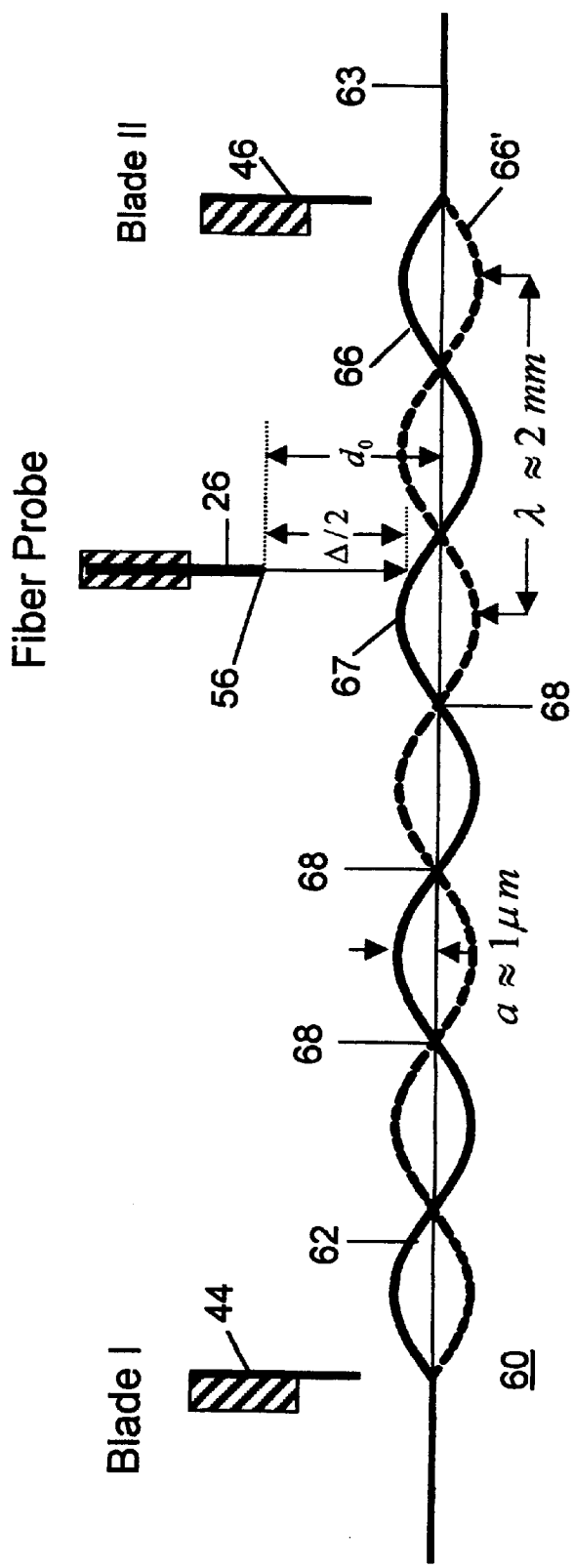
FIG. 2 is a greatly enlarged schematic representation of a pair of wave generating blades and two fiber optic probes located above and near the surface of a fluid on which a standing capillary wave has been established.
Figure 4:
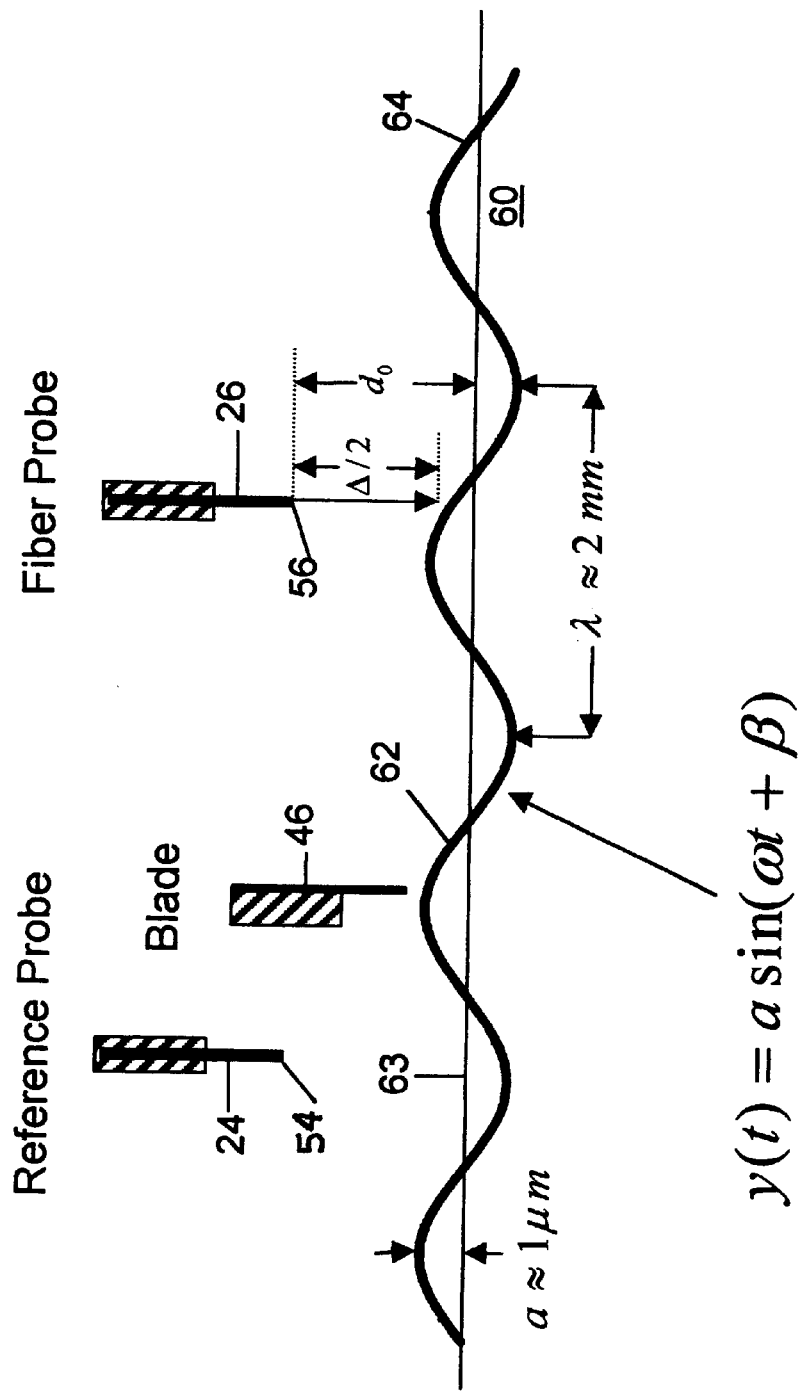
FIG. 4 is a greatly enlarged schematic representation of a wave generating blade and two fiber optic probes located above and near the surface of a fluid on which a traveling capillary wave has been generated.

FIG. 1 illustrates the system invention in a schematic diagram. A signal generator 40 which generates a sine wave of selected frequency is coupled to a solid-state blade driver 42 which amplifies the sine wave to about 100 volts AC. The amplified sine wave may be biased with a suitable DC voltage such that the amplified sine wave never declines below a positive potential. The signal generated by blade driver 42 is coupled to either first and second metallic blades 44, 46 or to both. Referring additionally to FIGS. 2 and 4 it can be seen that each blade 44, 46 is positioned above and very near (preferably within a few tenths of a millimeter) the top surface 62 of fluid 60 in vessel 28 and the blades 44, 46 are mounted substantially parallel. The fluid 60 is held at ground potential. The alternating electric field under each of first and second blades 44, 46 generates two capillary wave trains which recede from the blades 44, 46 on the two sides of each. Typically the amplitude of these capillary waves 64 is of the order of one micrometer. When both first and second blades 44, 46 are energized with a common sinusoidal voltage, a standing capillary wave 66 will be generated on the surface 62 of the fluid 60. Blades 44, 46 may be moved to achieve a horizontal spacing between them of a one-half odd integer wavelength such that a standing capillary wave 64 may be created between blades 44, 46 while the waves generated by the blades 44, 46 will interfere destructively exterior to the region between blades 44, 46.

A laser 10 is operative to generate a polarized light beam 8 which may be within or without the visible spectrum. The laser light beam 8 is transmitted through air or a fiber optic transmission element such as fiber optic cable to a first beam splitter 18 wherein a portion of the laser light 73 is siphoned to a reference amplifier/detector 38 via beam spreading lens 52. The reference amplifier/detector 38 detects fluctuations in the laser beam 8 due to small variations in line voltage or due to temperature drifts. Reference amplifier/detector 38 provides a reference signal to each of first and second detection units 48, 49 such that variations in the output of laser 10 will be normalized to cancel effects of line voltage and temperature variation. The main part of the laser light passes through first beam splitter 18 and is passed to Faraday isolator 12, a magneto-optic device which changes the polarization of laser light passing through it. The altered light beam 9 exiting Faraday isolator 12 is split into two altered beams 72, 74 by second beam splitter 15. As an alternative to the arrangement of beam splitters 18 and 15 and Faraday isolator 12, an acousto-optic modulator may be used to isolate the laser 10 from laser light reflected from downstream components and to split the beam into two off-axis beams and a center beam. In this case the center beam is used as the reference beam 73, while the two off-axis beams provide beams 72, 74. An acousto-optic modulator isolates input from output by slight frequency shifting of the output beams from the input beam.

The two deflected beams 72, 74 are directed through mirrors 14, 16 into fiber optic cables 30, 32 via graded index lenses 17, 19 and pass to first and second fiber optic couplers 20, 22 respectively, each of which is coupled to one of fiber optic probes 24, 26.

Fiber optic probes 24, 26 are disposed laterally to each of blades 44, 46 respectively, each being disposed substantially perpendicularly to the equilibrium surface 63 of fluid 60 in vessel 28. Each fiber optic probe 24, 26 is mounted such that it may be moved horizontally independent of the other of fiber optic probes 24, 26 and independent of each of blades 44, 46. First fiber optic probe 24 may remain stationary while second fiber optic probe 26 is moved laterally while mapping the profile of a traveling or standing capillary wave 64 on the fluid surface 62.

The laser light passing through first fiber optic cable 30 to first fiber optic coupler 20 is split into two beams. One beam is directed into first optical transmission line 34 which preferably is a fiber optic cable. The other beam is directed into first coupling line 35 which preferably is a fiber optic cable. The laser light transmitted along first optical transmission line 34 enters first fiber optic probe 24 where some of the laser light is transmitted through cleaved end terminus 54 toward the top surface 62 of the fluid 60 present in vessel 28. As the laser light emanating from terminus 54 strikes the top surface 62 of fluid 60, it reflects toward terminus 54 and reenters first fiber optic probe 24 and is conveyed along first fiber optic transmission line 34 where it is coupled by first fiber optic coupler 20 to first coupling line 35 to first detection unit 48. Some of the laser light received by fiber optic probe 24 is reflected by terminus 54 and reflects into first optic transmission line 34 and also passes through first fiber optic coupler 20 to first detection unit 48. Similarly a portion of laser light traveling along second optical transmission line 36 reflects from terminus 56 of fiber probe 26 and another portion is reflected from the surface 62 of the fluid 60 back into the fiber probe 26. The light reflected by the fluid surface 62 and by the terminus 54 of fiber optic probe 24 forms an interference pattern within first optic transmission line 34 and first coupling line 35 that is sensitive to the length of the gap between the terminus 54 and the top surface 62 of fluid 60. In an identical fashion the light reflected by terminus 56 and from the top surface 62 of fluid 60 below second fiber optic probe 26 creates an interference pattern in second optical transmission line 36 and second coupling line 37 which accurately reflects the variation in gap between terminus 56 and fluid surface 62 below terminus 56.

Each of detection units 48, 49 detects the interference pattern in first and second coupling lines 35, 37 respectively. Hence detector 48 will detect the interference pattern created by the reflection from terminus 54 and the reflection from the wave surface 62 of fluid 60 received by first fiber optic probe 24 while detector 49 detects the interference pattern created by the reflection from terminus 56 and the reflection from the wave surface 62 of fluid 60 received by first fiber optic probe 26. Each of detection units 48, 49 is coupled to digital oscilloscope 50 which will display the pattern of fringes of the detected interference pattern detected by detection units 48, 49.

FIG. 2 is a schematic representation of blades 44, 46 and fiber optic probe 26 in position above fluid 60. To obtain dispersion data for the fluid 60, a standing capillary wave is established on the fluid surface 62. Blades 44, 46 are coupled together as shown in FIG. 1 such that each blade 44, 46 excites the surface 62 of fluid 60 with the same DC-biased electromagnetic sine wave. The amplitude of standing capillary wave 66 has been vastly exaggerated in FIG. 2 for clarity. The two blades 44, 46, are separated by a few centimeters and are excited by sine wave voltage of the same phase, amplitude, and frequency. Each of blades 44, 46 is positioned at substantially the same small distance (a few tenths of a millimeter) above the surface 62 of the fluid 60. Since each blade 44, 46 sends a wave train toward the other, a standing capillary wave 66 is established on the water surface 62 between the two blades 44, 46. If the distance between the two blades 44, 46 is chosen to be a half odd-integer wavelength, the two wave trains interfere destructively on the outer sides of the blades 44, 46. This judicious choice of the blades 44, 46 separation produces a region of standing waves 66 between the blades 44, 46 while the surface of fluid 60 outside the blades 44, 46 remains calm. Measurement of the distance between several nodes 68 of standing wave 66 yields the wavelength of the standing capillary wave 66. The solid curved line of FIG. 2 shows the standing capillary wave 66 at the time when the amplitude is at its maximum while the dashed curved line of FIG. 2 shows standing capillary wave 66 at the opposite phase in its cycle. Nodes 68 are points where the amplitude of the standing wave 66 is zero. The distance between nodes 68 is equal to one-half wavelength of the standing capillary wave 66.

In the instant invention, at least one of fiber optic probes 24, 26 is attached to a micropositioner, which in turn is equipped with a digital micrometer. This enables measurement of the wavelength of the standing capillary waves 64 routinely to within a micrometer. A precise dispersion relation is obtained by a measurement of the wavelength at various frequencies. For instance, second fiber optic probe 26 may be mounted on an electronic micrometer (not shown), which records the horizontal position of fiber optic probe 26 with an accuracy of one micron. A typical wavelength is about two millimeters, and typical wave amplitudes are less than one micron. Because second fiber optic 26 probe is laterally moveable on a micropositioner, second fiber optic probe 26 may detect the presence of nodes 68 on the standing capillary wave 66 by the absence of an interference pattern at the nodes. Thus the distances between nodes 68 may be measured accurately.

As second fiber optic probe 26 is moved laterally from one node to the next in several small steps, the interference pattern records, at each step, the maximum oscillation of the surface under the probe. The vertical fluid oscillation is zero at the nodes 68 but increases as the probe moves toward the antinodes 67. Thus the profile of the standing capillary wave may be mapped point by point between two nodes.

Blades 44 and 46 are optimally laterally spaced at a distance equal to one-half odd integer wavelength so that, outside the space between first blade 44 and second blade 46 the waves generated by blades 44, 46 will interfere destructively to create a calm surface, thereby preventing reflections from affecting the standing capillary wave 66. The frequency of the sine wave on blades 44, 46 may be varied and the wavelength A of the standing capillary wave 66 at each of a range of frequencies may be determined for later reference. In practice, it is found that a blade spacing of approximately five centimeters provides a suitable separation when the distance between nodes 68 is about one millimeter and the wavelength A of the standing capillary wave 66 is approximately two millimeters. The amplitude of the standing capillary wave 66 is typically about one micron.

Figure 3:
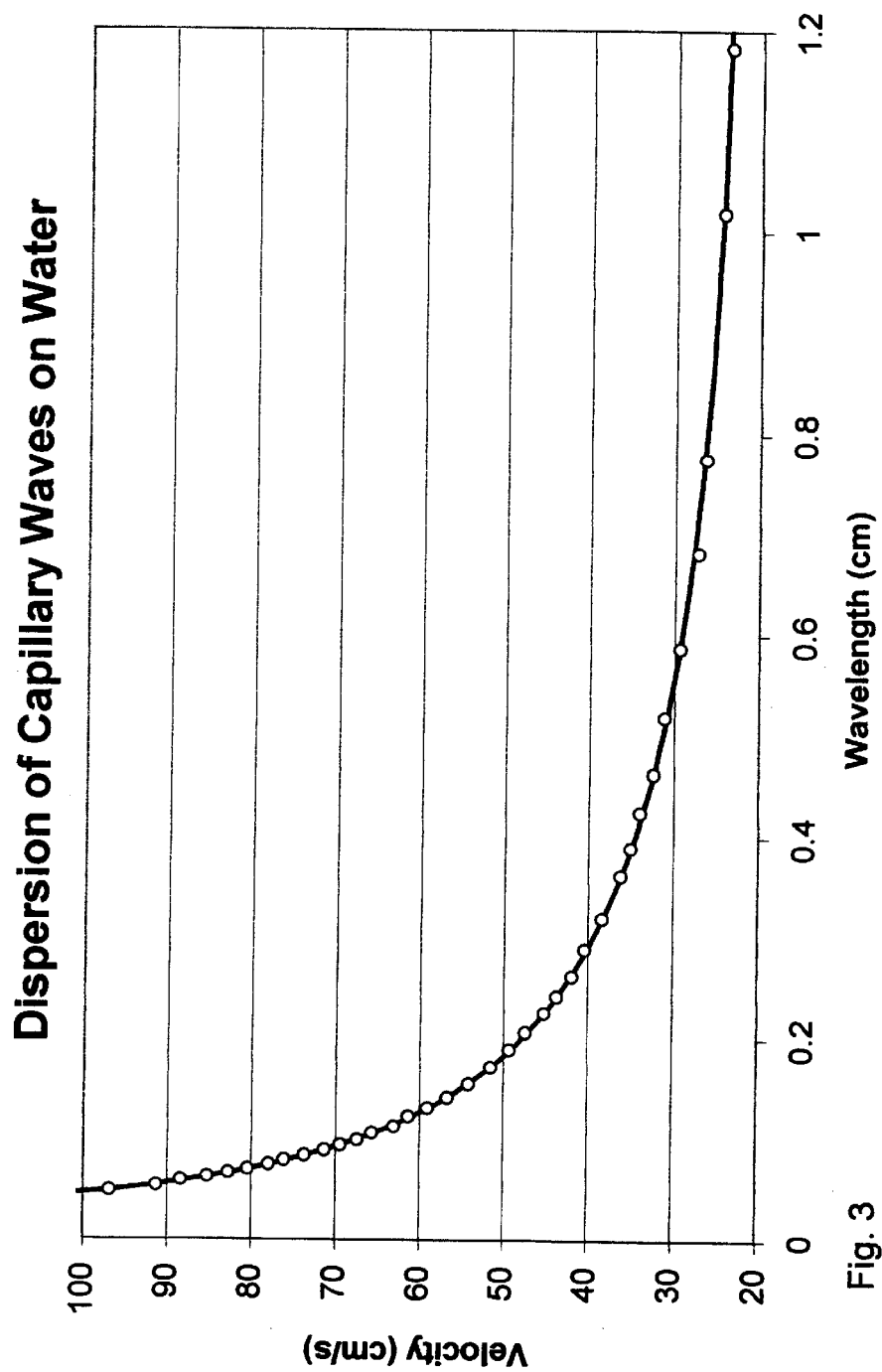
FIG. 3 is a graph showing data points of the phase velocity of capillary waves on water at 20° C. as a function of wavelength, as determined with the apparatus of FIG. 1, with a solid line plotting the theoretical dispersion relation of surface waves on water.

FIG. 3 shows the phase velocity of capillary waves on water at 20° C. as a function of wavelength obtained by this method. The solid line is a plot of the simplified dispersion relation of surface waves on water given by, $$v_\phi = (g\lambda/2\pi + 2\pi\sigma/\lambda\rho)^{1/2} \quad \text{(Eq. 1)}$$

where $v_\phi$ is the phase velocity, g is the acceleration of gravity, $\lambda$ is the wavelength, $\sigma$ is the surface tension, and $\rho$ is the fluid density. We use the widely accepted values of the parameters Car (72.8 dyn/cm) and $\rho$ (0.9982 gm/cm$^3$) for pure water at 20° C. to plot the solid line in FIG. 3.

Conversely, the dispersion data may be fit to Eq. 1 to obtain the surface tension when the density of the fluid is known.

FIG. 4 is a schematic representation of the arrangement of apparatus for the second stage of the invention method to determine fluid viscosity. First fiber optic probe 24 is stationed at a fixed position above fluid 60, laterally spaced from blade 46 which is positioned at a fixed horizontal location above fluid 60 a few tenths of a millimeter above the equilibrium surface 63 of fluid 60. A second blade is not utilized in this stage of the method. Blade 46 carries a DC-biased sine wave voltage approximately 100 VAC which excites the equilibrium surface 63 of fluid 60 creating a traveling capillary wave 64 on fluid 60 which travels away from blade 46 in either direction. The amplitude of traveling capillary wave 64 has been vastly exaggerated in FIG. 4 for clarity.

Second fiber optic probe 26 is also positioned near the surface of fluid 60 such that laser light from the terminus 56 thereof will be directed toward fluid 60 and be reflected from the wave surface 62 of traveling capillary wave 64. A portion of the laser light directed toward terminus 56 will reflect from terminus 56 and both reflections will create an interference pattern within second optic transmission line 36.

Second fiber optic probe 26 is carried on a micropositioner equipped with an electronic micrometer (not shown), which records the horizontal position of fiber optic probe 26 above the wave surface 62 as second fiber optic probe 26 is moved laterally. The electronic micrometer measures the distance moved by second fiber optic probe 26 with an accuracy of one micron.

The distance from terminus 56 of the second fiber optic probe 26 to the equilibrium surface 63 is $d_o$, and the roundtrip distance between the terminus 56 of the second fiber optic probe 26 and the wave surface 62, i.e., the path difference between the internally reflected beam and the beam reflected by the wave surface 62, is $\Delta$. Second fiber optic probe 26 is moved laterally and is used to detect the wave amplitude of the traveling capillary wave 64 as it moves past horizontal points at selected locations horizontally spaced from blade 46. Therefore, second fiber optic probe 26 will detect the attenuation in the amplitude of the traveling capillary wave 64 as it travels away from the blade 46. First fiber optic probe 24 remains in a fixed location near blade 46 in order to detect any change in the wave amplitude due to changes in the equilibrium surface level 63 of fluid 60 due to evaporation.

Figure 5:
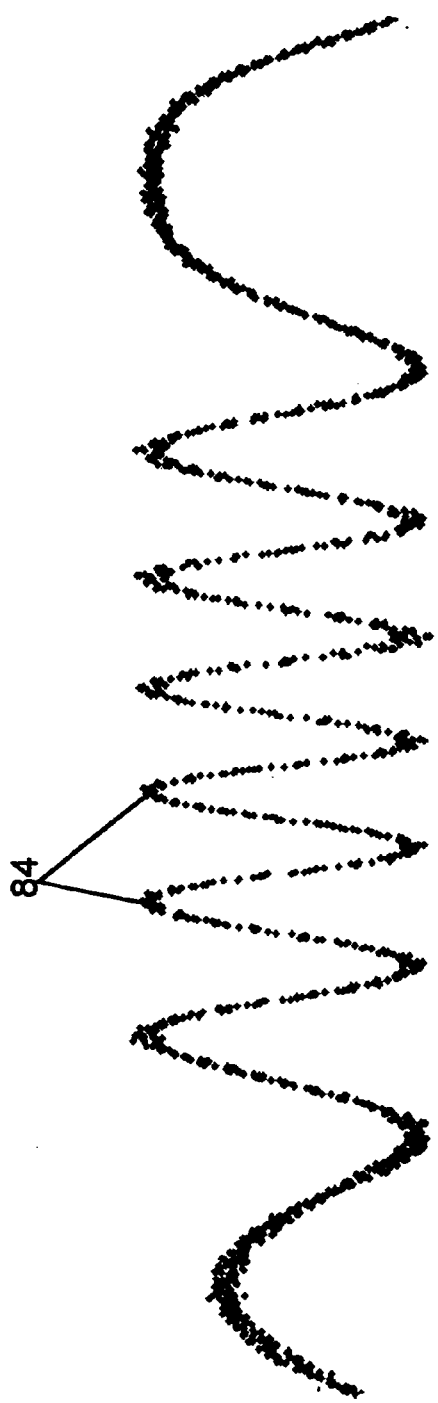
FIG. 5 is an oscillographic trace of a raw interference signal for a half period as received from the Detection/Processing/Amplification unit of the invention.

FIG. 5 shows a typical raw interference pattern taken directly from the photo detector of either of detection units 48, 49 as displayed on the digital oscilloscope 50.

Figure 6:
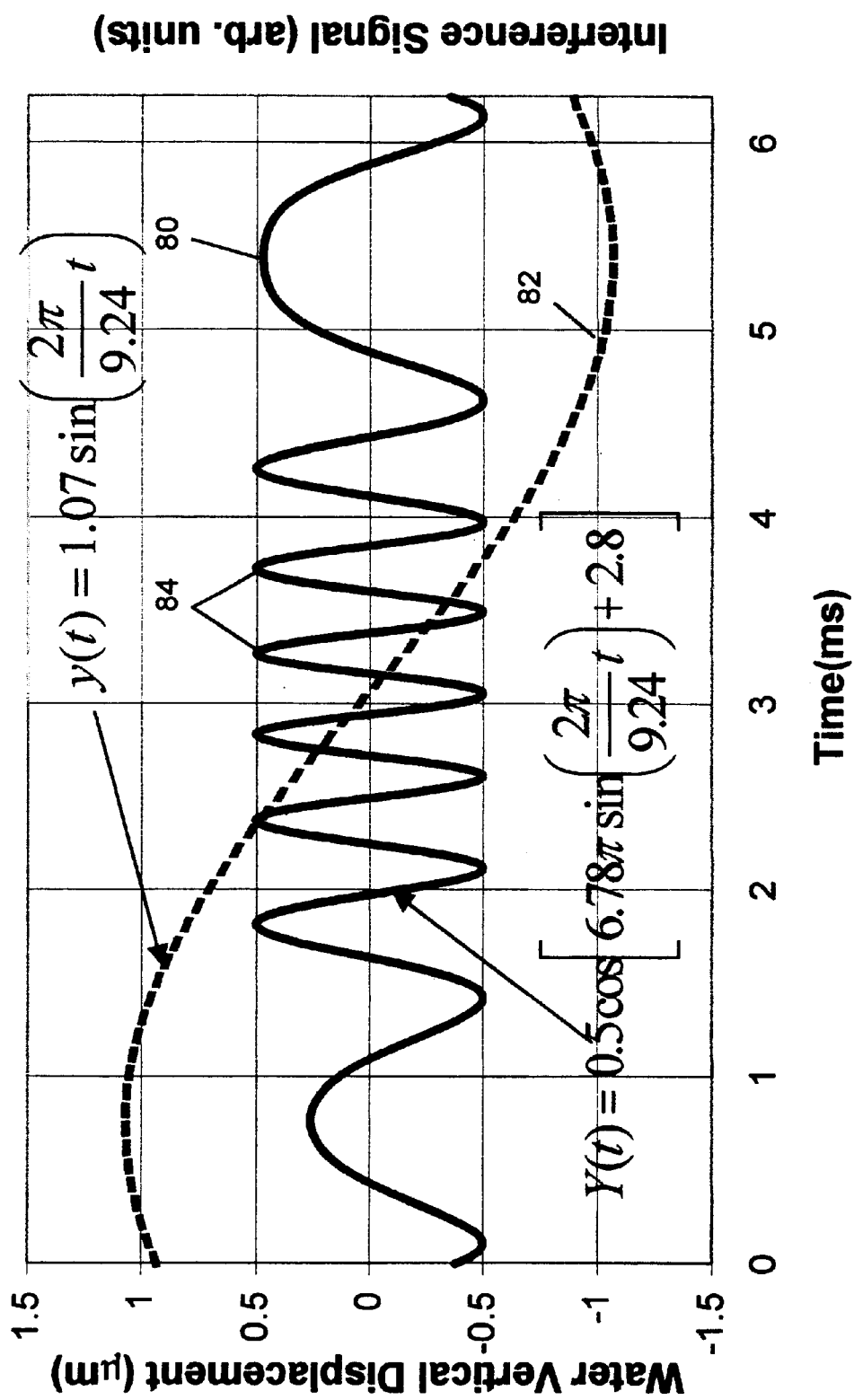
FIG. 6 is a graph of a mathematically fit solid curve which replicates the oscillographic trace of FIG. 5. A dashed curve on the grid depicts the vertical displacement of the water wave under the probe as a function of time.

FIG. 6 is a graph of fluid vertically displaced over time corresponding to the interference pattern of FIG. 5. The solid curve 80 of FIG. 6 is a mathematical fit to the scope trace of FIG. 5, and the dashed curve 82 of FIG. 6 is the surface capillary wave 64 that produced the interference pattern. Since there is a one-to-one correspondence between the surface capillary wave 64 and the resulting interference pattern of FIG. 5, the profile of the surface capillary wave 64 can be recovered by an analysis of the interference pattern. Indeed, as discussed later, the number of fringes 84 in the interference pattern is directly proportional to the amplitude of the surface capillary wave 64. For the pattern shown in FIG. 4, the number of fringes is 6.78 and the amplitude of the wave is 1.07 micrometer.

After precise measurement of the separation of nodes on the standing wave 66, at varying excitation frequencies, one of blades 44, 46 is decoupled such that only one blade, for example, blade 46, is coupled to sine wave generator 40 and this blade generates a traveling capillary wave 64 on surface 63. One of fiber optic probes 24, 26, for instance, first fiber optic probe 24, is left stationary near blade 46 while second fiber optic probe 26 is moved laterally to measure the amplitude and profile of the traveling capillary waves 64 as they travel away from blade 46 and attenuate in amplitude.

To determine the wave amplitude of a traveling wave from the interference record, the vertical oscillation of the water surface under either fiber optic probe 24, 26 may be represented by $$y(t) = a \sin(\omega t + \beta) \quad (\text{Eq. 2})$$

where a is the wave amplitude, $\omega$ is the angular frequency, t is the time, and $\beta$ is a phase which depends only on the position of the probe relative to the blade position. If $d_o$ is the air gap between one of fiber optic probes 24, 26 and the equilibrium surface 63 of the water, then the path difference between the two reflected beams is $$\Delta = 2[d_0 - a \sin(\omega t + \beta)]. \quad (\text{Eq. 3})$$

Thus, the ac component of the resulting interference pattern is given by, $$Y(t) = A \cos[(2\pi\Delta/\lambda_1) + \pi] \quad (\text{Eq. 4})$$

Here A is the amplitude of the interference signal, $\lambda_1$ is the wavelength of the laser light, and $\pi$ is added to the phase to account for the fact that the light beam reflecting from the water surface suffers a phase shift of $\pi$ radians. When Eq. 3 is substituted in Eq. 4, the result is, $$Y(t) = A \cos\{(4\pi/\lambda_1)[d_o - a \sin(\omega t + \beta)] + \pi\}, \quad (\text{Eq. 5})$$

which simplifies to, $$Y(t) = A \cos[b \sin(\omega t + \beta) - \phi]. \quad (\text{Eq. 6})$$

Here b stands for $4\pi a/\lambda_1$, and $\phi$ is a phase angle given by $$\phi = (\pi + 4\pi d_o/\lambda_1). \quad (\text{Eq. 7})$$

The relationship between a and b determines the relation between the wave amplitude and the number of fringes in the interference signal. Thus, $$a = b\lambda_1/4\pi. \quad (\text{Eq. 8})$$

To determine the amplitude of the capillary wave from the interference data, it is only necessary to extract the parameter b from the data to use in Eq. 8. This is achieved by fitting the analytical expression in Eq. 6 to the interference data. To accomplish this, the interference pattern shown in FIG. 4 is digitized and used as input in a multi-variable fit routine, which adjusts the four parameters of Eq. 6 until a good fit is achieved. Indeed, of the four parameters in Eq. 6, A and $\beta$ are readily available from the raw data, so the fit routine reduces to a search in the two-parameter space of b and $\phi$. By this method we determine the attenuation of the wave amplitude as a function of the distance traveled from the source.

Wave attenuation must then be related to viscosity. The dissipation of wave energy due to viscosity manifests itself in the attenuation of the amplitude as the wave travels along the surface. Indeed, in the linear limit, the rate of energy loss is proportional to the wave energy and is given by $$dE/dt = -(4k^2\eta/\rho)E, \quad (\text{Eq. 9})$$

where E is the wave energy per unit surface area, $\eta$ is the fluid viscosity, $\rho$ is the fluid density, and $k = 2\pi/\lambda$ is the wave number. Since the wave energy is proportional to the square of its amplitude, we can immediately write Eq. 9 in terms of the wave amplitude, $$da/a = -(2k^2\eta/\rho)dt. \quad (\text{Eq. 10})$$

Equation 10 implies that the fractional loss of the wave amplitude is proportional to the elapsed time. Since in a time interval dt the wave train travels a distance $dx = v_g dt$, where $v_g$ is the group velocity, Eq. 10 can be recast into $$da/a = -(2k^2\eta/\rho)dx/v_g, \quad (\text{Eq. 11})$$

which immediately yields, $$a = a_o e^{-\alpha x} \quad (\text{Eq. 12})$$

with $\alpha$, the attenuation coefficient, given by $$\alpha = (2k^2\eta/\rho v_g). \quad (\text{Eq. 13})$$

For capillary waves on deep water the group velocity $v_g$ is given by $$v_g = (g + 3\sigma k^2/\rho)/2(gk + \sigma k^3/\rho)^{1/2}. \quad \text{(Eq. 14)}$$

When Eq. 14 is used in Eq. 13, we obtain the viscosity in terms of four measurable quantities, namely, wave number $k = 2\pi/\lambda$, surface tension $\sigma$, density $\rho$, and the attenuation coefficient a. Indeed, we have $$\eta = [\alpha\rho/2k^2][(g + 3\sigma k^2/\rho)/2(gk + (gk + \sigma k^3/\rho)^{1/2}]. \quad \text{(Eq. 15)}$$

The attenuation coefficient $\alpha$ is obtained from a plot of the wave amplitude vs. the distance from the blade. Often the ratio of $\eta/\rho$ is referred to as quoted in the literature as the kinematic viscosity. FIG. 7 gives the wave amplitude vs. distance from the source. To obtain this data two fiber optic probes 24, 26 are utilized, one stationary (e.g. fiber optic probe 24) and the other horizontally moveable (e.g fiber optic probe 26). The amplitude data obtained by the moveable second fiber optic probe 26 is a function of position and is normalized by that obtained from the stationary first fiber optic probe 24 to account for any change in the equilibrium water level 63 due to evaporation. While a small change in the water level has no effect on the detection system, it does affect the amplitude of the capillary waves 64 being generated under the blade 46. The normalization procedure outlined above eliminates this source of error. The solid graph in FIG. 7 is an exponential fit to the data and gives the attenuation coefficient a for use in Eq. 15.

EXAMPLE

The invention system has been employed to determine the kinematic viscosity of pure water over temperature to demonstrate the utility and accuracy of the system by comparing data published in the *CRC Handbook of Chemistry and Physics* (CRC, Cleveland, Ohio, 1999) with the empirical data provided by this invention apparatus and method. FIG. 8 gives our measured values of the kinematic viscosity, $\eta/\rho$, vs. the temperature for pure water. The solid line in the figure is a second order polynomial fit to the published data for pure water and is included for comparison. Since water has a very small viscosity to begin with, measuring the temperature variation of its viscosity constitutes a severe test of our method. The excellent results presented in FIG. 8 show that the non-contact method described provides a sensitive new alternative to flow viscometry. Furthermore, the non-contact nature of the method provides another clear advantage by eliminating the possibility of contamination of the fluid under study.

Having described the invention, I claim:

1. Apparatus for measuring characteristics of capillary waves on the surface of a fluid comprising two laterally spaced apart sine wave generators coupled together generating a standing wave on the surface of the fluid, the standing wave having nodes therealong, a laser coupled to an optic transmission line to pass laser light thereinto, the optic transmission line having a terminus disposed above and near the surface of the fluid to permit laser light to be directed substantially perpendicularly onto the surface, the terminus internally reflecting some laser light into the optic transmission line and receiving laser light reflected from the surface, a detector coupled to the optic transmission line to detect an interference pattern in the optic transmission line created by interaction of the reflected light from the surface and the light reflected by the terminus, the interference pattern responsive to the amplitude of the portion of the standing wave below the terminus, the terminus being continuously laterally moveable, a measurement element to measure lateral movement of the terminus, whereby the distance between nodes of the standing wave may be measured and the amplitude profile of the standing wave may be mapped.

2. The apparatus of claim 1 wherein the detector digitizes the interference pattern, a digital oscilloscope coupled to the detector to display the interference pattern, a computer is coupled to the oscilloscope.

3. The apparatus of claim 2 wherein the two sine wave generators are a pair of blades disposed substantially in parallel and located near the surface of the fluid.

4. The apparatus of claim 3 wherein the pair of blades is coupled to a signal generator generating sine waves of frequency in the range of 10 Hz to 1000 Hz and of amplitude of approximately 100 volts AC.

5. The apparatus of claim 4 wherein the pair of blades is spaced apart approximately ten centimeters, the optic transmission line being a fiber optic cable, the terminus being the cleaved end of the fiber optic cable, the measurement element measuring within one micron, the pair of blades spaced apart a distance equal to one-half of an odd integer multiple of the wavelength of the standing wave, whereby the surface is calm outside a region defined by the pair of blades.

6. The apparatus of claim 5 wherein one of the pair of blades may be selectively deenergized, the energized other of the pair of blades generating a traveling capillary wave on the surface of the fluid when the one of the pair of blades is deenergized, the terminus laterally moveable to determine the amplitude of the traveling capillary wave at varying distances from the energized other of the pair of blades.

7. The apparatus of claim 6 wherein a second optic transmission line having a terminus thereon is coupled to the laser and transmits laser light, the terminus of the second optic transmission line is positioned near the surface of the fluid and near the energized other of the pair of blades, a second detector is coupled to the second optic transmission line to detect an interference pattern in the second optic transmission line created by interaction of laser light reflected internally from the terminus of the second optic transmission line and by the surface of the fluid below the terminus of the second optic transmission line, the second detector responsive to the gap between the terminus of the second optic transmission line and the surface of the traveling wave beneath the terminus of the second optic transmission line, whereby evaporative changes of the fluid may be detected.

8. Apparatus for measuring viscosity of a fluid comprising two laterally spaced apart electromagnetic generators disposed above and near the surface of the fluid to generate surface waves on the surface of the fluid, the two electromagnetic generators selectively coupled together to generate a standing surface wave, a laser having a first optic transmission line coupled thereto, the first optic transmission line having a terminus thereon disposed above and near the surface of the fluid, the terminus disposed laterally between the two electromagnetic generators, a first photo detector coupled to the transmission line to detect optical energy within the transmission line, the first photo detector generating an interference signal in response to detection of the optical energy, the terminus being horizontally moveable over the surface of the fluid.

9. The apparatus of claim 8 wherein an oscilloscope is coupled to the photo detector to display the detected interference signal, a computer coupled to the oscilloscope, the computer produces a signal fitted to the display of the detected interference signal.

10. The apparatus of claim 8 wherein a second optic transmission line is coupled to the laser, the second optic transmission line having a terminus thereon disposed laterally between the two electromagnetic generators at a fixed position, the terminus of the second optic transmission line disposed above and near the surface of the fluid, a second photo detector coupled to the second optic transmission line to detect optical energy within the second optic transmission line, the second photo detector generating an interference signal in response to detection of the optical energy within the second optic transmission line, an oscilloscope coupled to the second photo detector to display the detected interference signals in the first optic transmission line and the second optic transmission line.

11. The apparatus of claim 8 wherein one of the electromagnetic generators is selectively deenergized, the energized other one of the electromagnetic generators generating a traveling capillary wave on the surface of the fluid, the terminus of the first optic transmission line laterally moveable to selected locations distant from the other energized one of the electromagnetic generators, whereby the amplitude of the surface waves may be measured near the energized one of the electromagnetic generators and at varying distances therefrom.

12. The apparatus of claim 8 wherein the electromagnetic generators comprise a sine wave generator coupled to two spaced apart metal blades disposed in parallel, the optic transmission line comprises a fiber optic cable.

13. The apparatus of claim 9 wherein the blades are spaced apart a distance equal to one-half of an odd integer multiple of the wavelength of the standing wave, whereby the surface is calm outside a region defined by the pair of blades.

14. The apparatus of claim 11 wherein a second optic transmission line is coupled to the laser, the second optic transmission line having a terminus thereon disposed adjacent the other energized one of the electromagnetic generators the terminus of the second optic transmission line disposed above and near the surface of the fluid, a second photo detector coupled to the second optic transmission line to detect optical energy within the second optic transmission line, the second photo detector generating an interference signal in response to detection of the optical energy within the second optic transmission line, an oscilloscope coupled to the second photo detector to display the detected interference signals in the first optic transmission line and the second optic transmission line.

15. A method for measuring the wavelength of capillary waves on a fluid comprising the steps of generating a standing capillary wave on the surface of the fluid, locating the nodes along the standing capillary wave using a laser interferometer, measuring the distance between adjacent nodes to determine the wavelength of the standing capillary wave.

16. The method of claim 15 wherein the standing capillary wave is generated by use of a pair of laterally spaced apart sine wave generators coupled together, the laser interferometer comprises a laser coupled to a fiber optic cable having a cleaved end disposed a short distance from the fluid surface, the fiber optic cable further coupled to a interference pattern detector, locating the nodes by moving the laser interferometer laterally over the standing capillary wave.

17. A method for measuring viscosity of a fluid comprising the steps of creating standing capillary waves on the surface of the fluid, using a movable laser interferometer to determine the distance between nodes of said standing waves, creating a traveling capillary wave on the surface of said fluid, using said laser interferometer to determine the amplitude of said traveling capillary wave as said traveling capillary wave moves along said surface, calculating viscosity from said distance and from said amplitude data.

18. The method of claim 17 wherein said standing capillary wave is generated by use of two spaced apart sinusoidal voltage carrying blades spaced a small distance above the surface of said fluid, said moveable laser interferometer comprises a laser coupled to a fiber optic probe having an end, the fiber optic probe emitting laser light from the end thereof toward said surface of said fluid, said fiber optic probe receiving light reflected from said surface of said fluid, said end of said probe reflecting some laser light along said probe, said probe coupled to a detector which detects an interference pattern in said probe, said traveling wave is generated by use of a single sinusoidal voltage carrying blade spaced a small distance above the surface of said fluid, said amplitude is calculated from said interference pattern in said fiber optic probe.

19. The method of claim 18 further including the steps of measuring the movement of the laser interferometer to within one micron, displaying the interference pattern on a digital oscilloscope, fitting the displayed interference pattern to a formula by use of a computer.

20. A method for determining the attenuation of a traveling capillary wave on a fluid surface comprising the steps of generating a traveling capillary wave on the fluid surface at a fixed location, using a laterally moveable laser interferometer to determine the amplitude of the traveling capillary wave at varying locations distant from the fixed location.

21. Apparatus for measuring amplitude damping of capillary waves on the surface of a fluid comprising a sine wave generator disposed at a fixed location above the surface of the fluid generating a capillary wave on the surface of the fluid, a laser coupled to an optic transmission line to pass laser light thereinto, the optic transmission line having a terminus disposed above and near the surface of the fluid to permit laser light to be directed substantially perpendicularly onto the surface, the terminus internally reflecting some laser light into the optic transmission line and receiving laser light reflected from the surface, a detector coupled to the optic transmission line to detect an interference pattern in the optic transmission line created by interaction of the reflected light from the surface with the light reflected by the terminus, the interference pattern responsive to the amplitude of the portion of the capillary wave below the terminus, the terminus laterally moveable to determine the amplitude of the capillary wave at varying distances from the fixed location of the sine wave generator, whereby an amplitude profile of the capillary wave may be mapped.

22. The apparatus of claim 21 wherein the amplitude of the capillary wave may be mapped as a function of distance from the sine wave generator, and an attenuation coefficient of the capillary wave may be determined, the attenuation coefficient useful to determine viscosity of the fluid.

23. The apparatus of claim 21 wherein a second optic transmission line having a terminus thereon is coupled to the laser and conveys laser light, the terminus of the second optic transmission line positioned near the surface of the fluid and near the fixed location of the sine wave generator, a second detector coupled to the second optic transmission line to detect an interference pattern in the second optic transmission line created by interaction of laser light reflected internally from the terminus of the second optic transmission line with light reflected by the surface of the fluid below the terminus of the second optic transmission line, the interference pattern of the second optic transmission line responsive to the amplitude of the portion of the capillary wave below the terminus of the second optic transmission line, the amplitude measured by the first detector normalized by the amplitude measured by the second detector, whereby any evaporative changes of the fluid may be rendered immaterial in determining an attenuation coefficient, and viscosity of the fluid may be determined accurately.

* * * * *

UNITED STATES PATENT AND TRADEMARK OFFICE
CERTIFICATE OF CORRECTION

PATENT NO.  : 6,563,588 B2
DATED       : May 13, 2003
INVENTOR(S) : Feredoon Behroozi It is certified that error appears in the above-identified patent and that said Letters Patent is hereby corrected as shown below:

Column 6,
Lines 28 and 33, delete "A" and substitute therefor -- $\lambda$ --.
Line 46, delete "Car" and substitute therefor -- $\sigma$ --.

Column 9,
Line 29, delete "a" and substitute therefor -- $\alpha$ --.

Signed and Sealed this

Eleventh Day of November, 2003

JAMES E. ROGAN
*Director of the United States Patent and Trademark Office*